US00PP16863P3

(12) United States Plant Patent

Misato et al.

(10) Patent No.: US PP16,863 P3

(45) Date of Patent: Jul. 25, 2006

(54) *BIDENS* PLANT NAMED 'SUNBIDESUPA'

(50) Latin Name: *Bidens ferulifolia*
Varietal Denomination: Sunbidesupa

(75) Inventors: Tomoya Misato, Omihachiman (JP); Kiyoshi Miyazaki, Hikone (JP)

(73) Assignee: Suntory Flowers Limited, Tokyo (JP)

( * ) Notice: Subject to any disclaimer, the term of this patent is extended or adjusted under 35 U.S.C. 154(b) by 17 days.

(21) Appl. No.: 10/810,046

(22) Filed: Mar. 26, 2004

(65) Prior Publication Data

US 2005/0216986 P1 Sep. 29, 2005

(51) Int. Cl.
*A01H 5/00* (2006.01)

(52) U.S. Cl. ..... Plt./263

(58) Field of Classification Search ..... Plt./263
See application file for complete search history.

(56) References Cited

FOREIGN PATENT DOCUMENTS

JP PBR 13269 7/2001

OTHER PUBLICATIONS

The Seed Catalogue 2004, Published 2003, 2 pgs., Thompson & Morgan, UK (Explanations for IDS Document).

Flower & Green, the newest catalog 2004, Published 2003; Suntory Flowers Ltd., 4 pages (partial English translation; Explanations for IDS Documents).

The 2004 Suntory Collection, Published 2003; Jackson & Perkins Wholesale, Inc.; 2 page (Explanations for IDS Documents).

Pineae Peak Performers featuring the 2004 Suntory Collection, Published 2003; Pineae Greenhouses, Inc; 3 pages (Explanations for IDS Documents).

Colour Wave Collection 2003–04, Published 2003; Ramm Botanicals Pty Ltd, 3 pages (Explanations for IDS Documents).

Colour Wave Collection 2003–04, Published 2002; Ramm Botanicals Pty Ltd, 3 pages (Explanations for IDS Documents).

*Primary Examiner*—Kent Bell
*Assistant Examiner*—Louanne Krawczewicz Myers
(74) *Attorney, Agent, or Firm*—Christie, Parker and Hale, LLP

(57) ABSTRACT

Disclosed herein is a new and distinct variety of *Bidens ferulifolia,* named 'Sunbidesupa' having a very compact and mounding growth habit with dense yellow green foliage. 'Sunbidesupa' has freely branching, stiff stems and very short internodes, dense yellow green foliage, and large, vivid-yellow inflorescences, with typically 8 ray florets in a whorl per inflorescence, on short peduncles. The plant exhibits good resistance to heat, cold, disease and pests.

2 Drawing Sheets

Botanical classification: *Bidens ferulifolia.*
Varietal denomination: 'Sunbidesupa'.

BACKGROUND OF THE VARIETY

The present invention relates to a new and distinct variety of *Bidens ferulifolia,* named 'Sunbidesupa'.

There are some *Bidens* varieties commercially available that have a spreading growth habit with vivid yellow flowers. These are suitable for naturalistic planting and for planting in containers throughout the summer until the first frost. However, there are few *Bidens* varieties that are stably compact.

Accordingly, this invention was aimed at obtaining a new *Bidens* variety with a compact and beautiful mounding habit having dense yellow green foliage and large vivid yellow flowers.

The parent variety 'Golden Eye' (unpatented) used in open-pollination to produce 'Sunbidesupa' is a cultivar having a compact growth habit and vivid yellow flowers.

The seeds of 'Golden Eye' are commercially available in the UK.

The new *Bidens* variety was discovered by the inventors in October 2000, within a population of seedling progeny from open-pollination of *Bidens ferulifolia* cultivar 'Golden Eye', that were made from April to October 1999 in Yokaichi-shi, Shiga-ken, Japan. The new *Bidens* was selected on the basis of its very compact and unique mounding growth habit, and for having dense yellow green foliage and large vivid yellow flowers. The selected plant was propagated by the use of cutting and grown in pots in a glasshouse and in the field in Yokaichi-shi, Shiga-ken, Japan, from April to November 2001. The botanical characteristics of the selected plant were examined, using a similar variety 'Innbid' (U.S. Plant Pat. No. 11,261) and 'Sunbideki' (unpatented). As a result, it was concluded that the selected new *Bidens* variety is distinguishable from any other variety whose existence is known to us and is uniform and stable in its characteristics. This new variety of *Bidens* plant was named 'Sunbidesupa'.

In the following description, the color-coding is in accordance with the Horticultural Colour Chart of The Royal Horticultural Society, London, England (R.H.S.).

SUMMARY OF THE VARIETY

This new variety is unlike any *Bidens* commercially available known to us as evidenced by the following unique combinations of characteristics.

1. Very compact and mounding growth habit with dense yellow green foliage.
2. Freely branching, having stiff stems and very short internodes.
3. Large, vivid yellow inflorescences on short peduncles.
4. Typically 8 ray florets per inflorescence.

The new variety 'Sunbidesupa' differs from the similar variety 'Innbid' in the following points.

1. 'Sunbidesupa' grows in a compact and mounding shape, while 'Innbid' grows in a broad and spreading shape.
2. The main stem of 'Sunbidesupa' is thicker than that of 'Innbid'.
3. The internode of 'Sunbidesupa' is shorter than that of 'Innbid'.
4. The diameter of the inflorescence of 'Sunbidesupa' is larger than that of 'Innbid'.
5. The average number of ray florets of 'Sunbidesupa' is 8, while that of 'Innbid' is 5.
6. The shape of the apex of the ray florets of 'Sunbidesupa' is sinuate, while that of 'Innbid' is acute.
7. The peduncle of 'Sunbidesupa' is shorter than that of 'Innbid'.

The new variety 'Sunbidesupa' differs from the similar variety 'Sunbideki' in the following points.

1. 'Sunbidesupa' grows in a compact and mounding shape, while 'Sunbideki' grows in a spreading shape.
2. The main stem of 'Sunbidesupa' is thicker than that of 'Sunbideki'.
3. The internode of 'Sunbidesupa' is shorter than that of 'Sunbideki'.
4. The diameter of the inflorescence of 'Sunbidesupa' is larger than that of 'Sunbideki'.
5. The color of the ray florets of 'Sunbidesupa' is vivid yellow (near R.H.S. 7A), while that of 'Sunbideki' is vivid yellow (near R.H.S. 15A) with vivid yellow (near R.H.S. 7A) margin.
6. The average number of ray florets of 'Sunbidesupa' is 8, while that of 'Sunbideki' is 5.
7. The peduncle of 'Sunbidesupa' is shorter than that of 'Sunbideki'.

This new variety of *Bidens* plant 'Sunbidesupa' was asexually reproduced by the use of cuttings in Yokaichi-shi, Shiga-ken, Japan, and the homogeneity and stability thereof were confirmed. The instant plant retains its distinctive characteristics and reproduces true to type in successive generations of asexual reproduction.

DESCRIPTION OF THE ILLUSTRATIONS

The depicted plants had been reproduced by the use of cuttings and were photographed July 2003 while growing outdoors in 20 cm pots at an age of approximately 4 months in Yokaichi-shi, Shiga-ken, Japan.

DESCRIPTION OF THE NEW VARIETY

Figure 1:
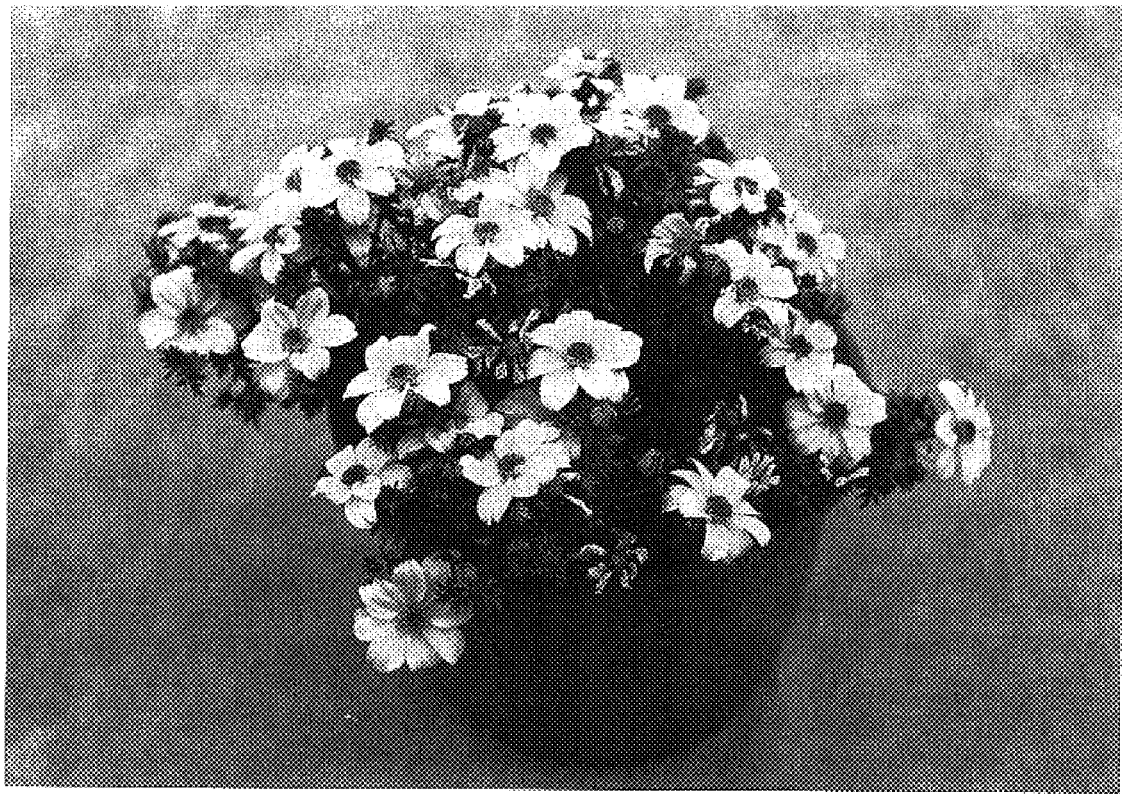
FIG. 1 illustrates a typical plant of the new variety of *Bidens* plant 'Sunbidesupa' while growing in a pot.
Figure 2:
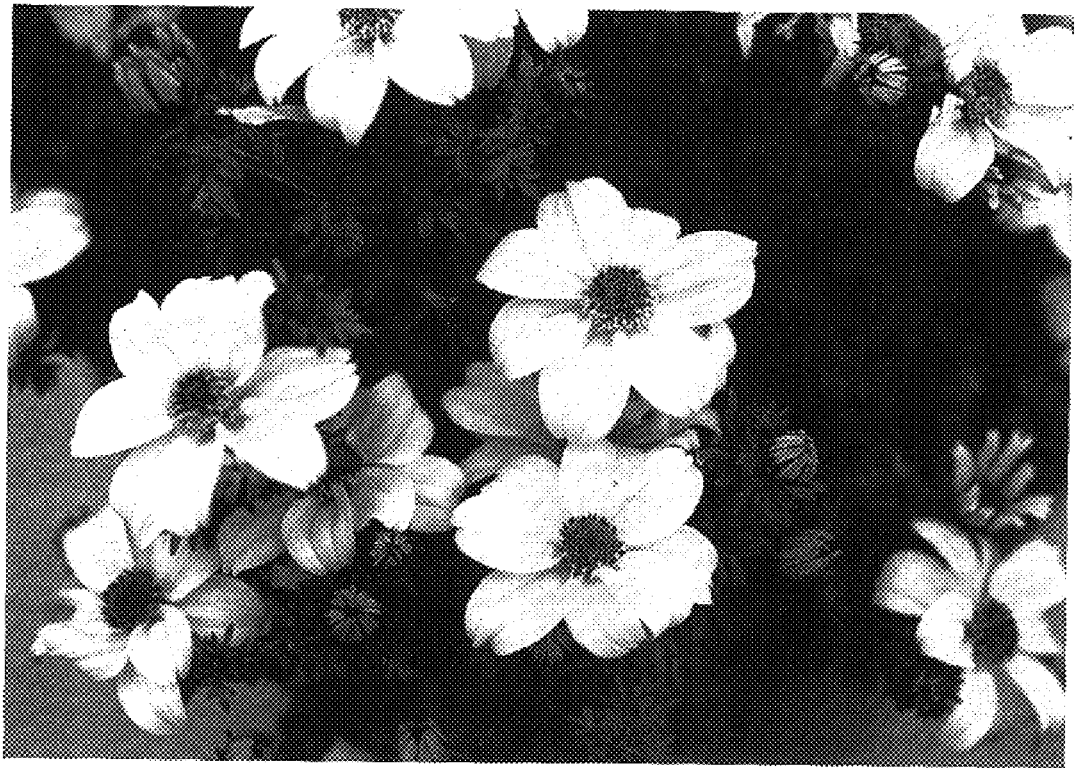
FIG. 2 illustrates a close view of typical foliage and blossoms of the new variety of *Bidens* plant 'Sunbidesupa'.

The botanical characteristics of the new and distinct variety of *Bidens ferulifolia* named 'Sunbidesupa' 4 months after cutting, as observed during May 2003 in Yokaichi-shi, Shiga-ken, Japan, are as follows:

Plant:
- *Growth habit.*—Very compact, mounding growth habit.
- *Plant height.*—Approximately 19 cm.
- *Spreading area of plant.*—Approximately 34 cm.

Stem:
- *Length.*—Approximately 20 cm.
- *Thickness.*—Main stem, approximately 3.7 mm.
- *Color.*—Near R.H.S. 187A(greyed-purple group).
- *Pubescence.*—Present.
- *Quantity of branching.*—Abundant. Freely branching.
- *Length of internode.*—Approximately 17 mm.

Leaf:
- *Arrangement.*—Opposite.
- *Length.*—Approximately 2.9 cm.
- *Width.*—Approximately 2.2 cm.
- *Shape/margin.*—Pinnatiparted; each segment is approximately 1.1 mm in width.
- *Venation.*—Pinnate venation. Color is near R.H.S. 144C (both sides).
- *Shape of apex.*—Acute.
- *Shape of base.*—Acuminate.
- *Color.*—Upper-side: Near R.H.S. 137C. Lower-side: Near R.H.S. 138B.
- *Length of petiole.*—Approximately 6.2 mm.
- *Diameter of petiole.*—Approximately 0.8 mm.
- *Color of petiole.*—Near R.H.S. 137C.
- *Texture.*—Smooth.

Inflorescence:
- *Number of inflorescences per plant.*—Approximately 60 inflorescences.
- *Type.*—Single, daisy-type composite inflorescence.
- *Diameter.*—Approximately 4.4 cm.
- *Depth.*—Approximately 1.0 cm.
- *Number of ray florets.*—Typically 8 in a single whorl.
- *Shape of ray floret.*—Elliptic.
- *Margin of ray floret.*—Entire.
- *Texture.*—Smooth.
- *Shape of apex of ray floret.*—Sinuate.
- *Shape of base of ray floret.*—Round.
- *Length of ray floret.*—Approximately 19.0 mm.
- *Width of ray floret.*—Approximately 13.5 mm.
- *Color of ray floret.*—Upper-side: Near R.H.S. 7A. Lower-side: Near R.H.S. 7A with near R.H.S. 166C venation.
- *Diameter of whole disc.*—Approximately 1.0 cm.
- *Length of disc floret.*—Approximately 6.1 mm.
- *Number of disc florets per inflorescence.*—Approximately 100.
- *Diameter of disc floret.*—Approximately 1.0 mm.
- *Texture of disc floret.*—Smooth.
- *Shape of disc floret.*—Tubular.
- *Diameter of involucre.*—Approximately 12.5 mm, about 26 phyllaries in three whorls.

Phyllaries:
- *Shape.*—Lanceloate.

*Length.*—Approximately 3.0 mm.
*Width.*—Approximately 1.0 mm.
*Shape of apex.*—Obtuse.
*Shape of base.*—Rotund.
*Margin.*—Entire.
*Texture.*—Smooth.
*Color.*—Near R.H.S. N200A.
*Color of disc floret.*—Near R.H.S. 14A.
*Fragrance.*—Absent.
*Peduncle.*—Approximately 1.3 mm in thickness, and 0.9 cm in length.
*Color of peduncle.*—Near R.H.S. 187A(greyed-purple group).
*Texture of peduncle.*—Smooth.

Buds:
*Diameter.*—Approximately 5.9 mm.
*Length.*—Approximately 6.9 mm.
*Shape.*—Globose.
*Color.*—Near R.H.S. 151C.

Reproductive organs:
*Androecium.*—Present on the disc florets only.
*Number of stamen.*—Five per disc floret.
*Anther shape.*—Elongated.
*Anther length.*—Approximately 1.8 mm.
*Anther color.*—Near R.H.S. 200B(brown group).
*Amount of pollen.*—Moderate.
*Pollen color.*—Near R.H.S. 14A(yellow-orange group).
*Gynoecium.*—Present on disc and ray florets.
*Pistil number.*—One per ray and disc floret.
*Pistil length.*—Approximately 5.5 mm.
*Stigma shape.*—Recurved, bipartite.
*Stigma length.*—Approximately 1.4 mm.
*Color of stigma.*—Near R.H.S. 14A(yellow-orange group).
*Style length.*—Approximately 4.0 mm.
*Style color.*—Near R.H.S. 3C(yellow group).
*Ovary color.*—Near R.H.S. 145C(yellow green group).
*Seed.*—Few seeds have been observed. The color of seeds is black, near R.H.S. N186A. Seeds are approximately 9 mm in length, 0.5 mm in width, and have two awns at the apex.
*Blooming period.*—Start at the beginning of April to the end of November in the southern-Kanto area, Japan. A bloom commonly lasts 6–7 days on the plant.

Physiological and ecological characteristics:
*Hardiness to cold.*—Good.
*Hardiness to heat.*—Good.
*Resistance to disease.*—Good.
*Resistance to pests.*—Good.

The new variety of *Bidens* plant is most suitable for hanging baskets, potted containers of all types, borders, and landscape.

It is claimed:

1. A new and distinct variety of *Bidens ferulifolia* plant named ‘Sunbidesupa’, substantially as herein illustrated and described.

* * * * *